United States Patent [19]

Braish

[11] Patent Number: 5,436,368
[45] Date of Patent: Jul. 25, 1995

[54] INTERMEDIATES IN THE PREPARATION OF 4,5-DIFLUOROANTHRANILLIC ACID

[75] Inventor: Tamim F. Braish, Ledyard, Conn.

[73] Assignee: Pfizer Inc., New York, N.Y.

[21] Appl. No.: 339,319

[22] Filed: Nov. 14, 1994

Related U.S. Application Data

[63] Continuation of Ser. No. 39,394, filed as PCT/US91/05171, Jul. 29, 1991, abandoned, which is a continuation of Ser. No. 606,666, Oct. 31, 1990, abandoned.

[51] Int. Cl.⁶ .......................................... C07C 229/58
[52] U.S. Cl. ................................................... 562/458
[58] Field of Search ........................................ 562/458

[56] References Cited

U.S. PATENT DOCUMENTS 4,954,639  9/1990  Fertel et al. .................... 562/456

*Primary Examiner*—José G. Dees
*Assistant Examiner*—Joseph M. Conrad
*Attorney, Agent, or Firm*—Peter C. Richardson; Paul H. Ginsburg; Grover F. Fuller, Jr.

[57] ABSTRACT

Compounds of the formula

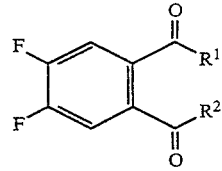

which are intermediates in the preparation of 4,5-difluoroanthranilic acid, an intermediate itself in the synthesis of quinolone antibacterials, and methods of preparing these intermediates.

5 Claims, No Drawings

INTERMEDIATES IN THE PREPARATION OF 4,5-DIFLUOROANTHRANILLIC ACID

This is a continuation of application Ser. No. 08/039,394, filed on Apr. 28, 1993, now abandoned, which is the National Phase of PCT/US91/05171 filed Jul. 29, 1991, which, in turn, was a continuation of Ser. No. 07/606,666 filed Oct. 31, 1990, now abandoned.

FIELD OF THE INVENTION

The present invention relates to compounds which are intermediates in the preparation of 4,5-difluoroanthranilic acid, an intermediate itself in the synthesis of quinolone antibacterials, and methods of preparing these intermediates.

BACKGROUND OF THE INVENTION

U.S. Pat. Nos. 4,571,396 and 4,861,779 disclose quinolone antibacterials which are synthesized using 4,5-difluoro-2-chlorobenzoic acid. 4,5-Difluoroanthranilic acid is a starting material for producing the 4,5-difluoro-2-chlorobenzoic acid used in the synthesis of these quinolones. These quinolones are useful in the treatment of bacterial infections of broad spectrum, particularly gram positive bacterial strains.

Synthesis of 4,5-difuoroanthranilic acid has been shown by G. McGraw, et al., *J. Chem. and Engineering Data*, 13,587 (1968) by nitrating 3,4-difluorobenzoic acid with a mixture of nitric and sulfuric acids to obtain 2-nitro-4,5-difluorobenzoic acid, the latter being reduced to obtain the desired compound. The 3,4-difluorobenzoic acid starting material, however, is expensive and difficult to obtain.

U.S. Pat. No. 4,833,270 also relates to the synthesis of 4,5-difluoroanthranilic acid by, first, reacting 3,4-difluoroaniline with hydroxylamine hydrochloride in the presence of chloral. The resulting intermediate is then cyclyzed using sulfuric acid to form 5,6-difluoroisatin. The 4,5-difluoroanthranilic acid is produced by oxidation of the aforementioned isatin with hydrogen peroxide. As before, however, 3,4-difluoroaniline is expensive and difficult to obtain.

U.S. Pat. Nos. 4,374,266 and 4,374,267 show a multi-step conversion process of 4,5-dichlorophthalic anhydride to 4,5-difluoroanthranilic acid. However, the processes are complex and involves the use of multiple reaction vessels.

SUMMARY OF THE INVENTION

The present invention relates to compounds of the formula

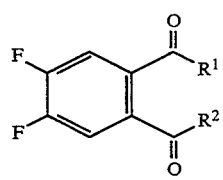

I wherein $R^1$ is O— X+, X is $NH_3OH$, an alkali metal, or an alkaline earth metal (such as K, Na, Li, Cs, or Ca) and $R^2$ is NHOH or $R^1$ and $R^2$ taken together to form the group

>N-OH

The present invention also relates to a method of preparing a compound of formula I wherein $R^1$ and $R^2$ are attached to the group

>N-OH comprising heating under vacuum a compound of formula I where $R^1$ is O— X+, X is $NH_3OH$, and $R^2$ is NHOH.

The present invention also relates to a method of preparing a compound of the formula

II comprising reacting the compound of formula I where $R^1$ is O— X+, $R^2$ is NHOH and X is $NH_3OH$ or $R^1$ and $R^2$ taken together to form the group

>N-OH and X is as defined for formula I with an alkyl or aryl sulfonyl chloride and excess base.

The present invention also relates to a method of preparing the compound of formula II in one reaction vessel comprising reacting the compound of the formula

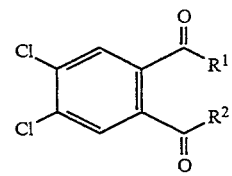

III wherein $R^1$ and $R^2$ are taken together for the group

>O with an earth metal fluoride to form a first reaction solution, reacting the first reaction solution with hydroxylamine to form a second reaction solution, and reacting the second reaction solution with an alkyl or aryl sulfonyl chloride and excess base.

DETAILED DESCRIPTION OF THE INVENTION

The following reaction scheme illustrates the preparation of the compounds of the present invention.

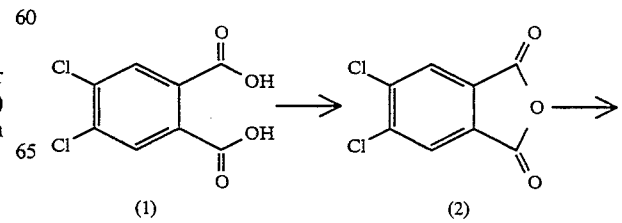

(1)            (2)

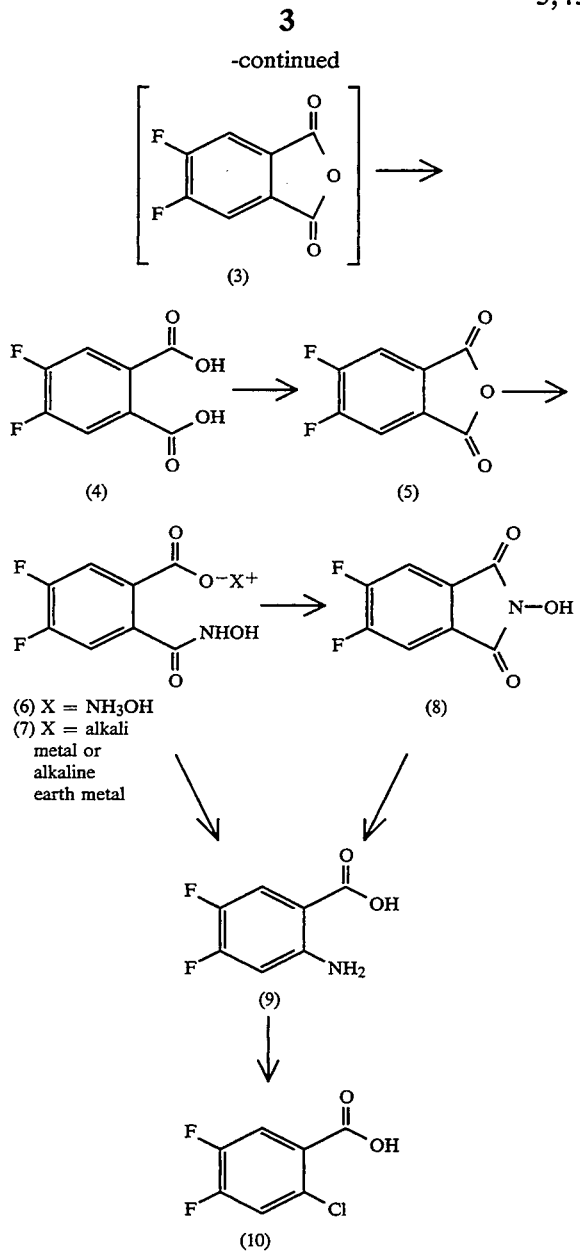

atmospheric pressure. The product in the solution is isolated as the corresponding diacid (4) by reacting the solution with water and a caustic base, such as sodium hydroxide or potassium hydroxide. The organic layer is then removed and the water layer acidified to form the diacid (4). Where the entire process is performed in one reaction vessel, this isolation step is not performed.

The 4,5-difluorophthalic acid (4) is converted to the corresponding anhydride (5) using the same procedure as was described previously for converting acid (1) to anhydride (2). After the formation of the anhydride (5), the anhydride ring is opened to produce the corresponding benzoate (6) by reacting (5) with from about 2 equivalents to about 3 equivalents of neutral hydroxylamine, preferably 2.2 equivalents. The reaction is carried out in base such as sodium methoxide or potassium hydroxide, preferably the latter, and can be carried out at a temperature at between about 0° C. and about 45° C., preferably room temperature, (about 27° C.).

The benzoate (6) can be converted to 4,5-difluoroanthranilic acid (9) by two routes. The first route involves treating the benzoate (6) with an alkyl or aryl sulfonyl chloride (about 2 to 3 equivalents, preferably 2 equivalents) and excess base (about 3:5 to 10 equivalents, preferably 4 equivalents). These bases such as alkali metal or alkaline earth metal hydroxide-type bases include NaOH, KOH, LiOH, Ca(OH)$_2$, and CsCO$_3$. Benzoate (6) is converted to metal benzoate intermediate (7) with cation X+ varying depending on the hydroxide-type base used. The process continues and metal benzoate intermediate (7) is converted to the difluoroanthranilic acid (9). p-Toluenesulfonyl chloride is the preferred sulfonyl chloride because of its crystallinity and ease of handling. The reaction can be conducted at between about −10° C. and about 50° C., preferably room temperature (about 27° C.).

The second route involves converting the benzoate (6) to N-hydroxy-4,5-difluorophthalimide (8). This is accomplished by heating the benzoate (7) to a temperature of between about 100° C. and 200° C., preferably 180° C., until the reaction is complete or about 45 minutes. This reaction takes place under aspirator vacuum of from about 0.1 to 100 Torr, preferably 15 Torr of mercury. The product is collected by sublimation to yield the desired compound. The imide (8) is then converted to the 4,5-difluoroanthranilic acid through the same reaction as was described above for converting the benzoate (7) to the desired acid (8) using the alkyl or aryl sulfonyl chloride and excess hydroxide-type base.

The 4,5-difluoroanthranilic acid (9) is converted to 2-chloro-4,5-difluoro benzoic acid (10) via diazotization an alkyl nitrate or an inorganic nitrite. Such alkyl nitrates include isoamylnitrate and t-butyl nitrate, preferably the latter. When an alkyl nitrate is used, an organic polar solvent should be used, such as dimethoxy ethane or acetonitrile, preferably the latter. When an inorganic nitrite, such as sodium nitrite, is used, water is the preferred solvent. Copper should also be used in either the organic or inorganic reaction solution. Copper (II) chloride, copper oxide, or copper bronze in hydrochloric acid can be used preferably copper (II) chloride.

The 2-chloro-4,5-difluorobenzoic acid can be converted into the aforementioned antibacterial compounds using methods described in European Patent Publication No. 0342849.

The antibacterial compounds may be administered alone in an admixture with a pharmaceutical carrier.

4,5-dichloro phthalic acid (1) available from the Aldrich Chemical Co. is converted to the corresponding anhydride (2) by heating (1) to between about 100° C. and about 150° C., preferably 138° C., under an inert atmosphere with a dialkyl anhydride, such as trifluoroacetic anhydride or acetic anhydride, or acetyl chloride, preferably the latter, in an inert solvent such as toluene or benzene, preferably toluene. A halogen-halogen exchange is performed on the 4,5-dichlorophthalic anhydride (2) to produce a 4,5-difluoro substituted version thereof (3) in solution. The reaction consists of reacting the dichloro compound (2) with an alkali metal fluoride such as NaF, KF, or CsF, preferably KF, most preferably spray dried KF. The ratio of fluoride to anhydride should be from about 2.5:1 to about 20:1, preferably 3:1. The halogen-halogen exchange is run at a temperature of between about 150° C. and about 220° C., preferably 185° C. The solvent used should be an aprotic solvent such as dimethylformamide, sulfolane, or dimethylsulfoxide, preferably sulfolane, at concentrations of from about 3.5:1 to about 10:1, preferably 4:1. The reaction can be run either in a pressure vessel or at Such a carrier should be selected with regard to the intended route of administration and standard pharmaceutical practice. Such antibacterial compounds can be administered orally or in the form of tablets containing such excipients as starch or lactose, or in capsules either alone or in an admixture with excipients, or in the form of elixirs or suspensions containing flavoring or coloring agents. In the case of animals, they are advantageously contained in an animal feed or drinking water in a concentration of 5 to 5000 ppm, preferably 25 to 500 ppm. They can also be injected parenterally, for example, intramuscularly, intravenously or subcutaneously. For parenteral administration, they are best used in the form of a sterile aqueous solution which can contain other solutes such as salts or glucose to make the solution isotonic.

The antibacterial compounds can be administered to animals intramuscularly or, subcutaneously at dosage levels of about 0.1 to 50 mg/kg/day, advantageously 0.2 to 10 mg/kg/day given in a single daily dose or up to 3 divided doses. The antibacterial compounds can be administered to humans for the treatment of bacterial-diseases by either the oral or parenteral routes, and may be administered orally at dosage levels of from about 0.1 to 500 mg/kg/day, advantageously 0.5 to 50 mg/kg/day given in a single dose or up to 3 divided doses. For intramuscular or intravenous administration, dosage levels are from about 0.1 to 200 mg/kg/day, advantageously 0.5 to 50 mg/kg/day. While intramuscularly administration may be a single dose or up to 3 divided doses, intravenous administration can include a continuous drip. Variations will necessarily occur depending on the weight and condition of the subject being treated and the particular route of administration chosen as will be known to those skilled in the art. The antibacterial activity of the compounds is shown by testing according to the Steer's replicator technique which is a standard in vitro bacterial testing method described by E. Steers et al., Antibiotics and Chemotherapy, 9. 307 (1959).

The present invention is illustrated by the following Examples, but in no way is it intended to be limited thereby.

EXAMPLE 1

4,5-Dichlorophthalic Anhydride (2)

200 g of 4,5-dichlorophthalic acid (851 mmol, M.W. 235) was suspended in 480 ml of acetic anhydride and the solution was heated to reflux for 5 hours. The solution was allowed to cool to room temperature over 2 hours, then cooled to 0° C. and filtered and washed with 100 ml of hexane and dried to provide the title compound with a 92% yield (170 g). M.P. 184° C.–186° C. $^1$H NMR(CDCI$_3$) : 8.1 (s).

EXAMPLE 2

4.5-Difluorophthalic Acid (4)

The title compound of Example 1 (50g, 230 mmol) was suspended in 200 ml of sulfolane and potassium fluoride (46.9 g, 810 mmol) was added and the solution was heated to 185° C. for 3 hours. After cooling the reaction, 1N NaOH solution was added to bring the solution to pH 14, and the solution was extracted with 4×100 ml of diethylether. The pH was then adjusted to 2.5 with 10% acqueous HCl and the solution was extracted with 4×75 ml of ethylacetate. The combined organic layers were dried over MgSO$_4$ and evaporated to give −41.1 g of the title compound (81% yield). $^1$H NMR(CDCI$_3$) : 7.86 (t). Combustion analysis for C$_8$H$_4$F$_2$O$_4$: C, 47.54; H, 1.99. Found: C, 47.21; H, 2.01.

EXAMPLE 3

4,5-Difluorophthalic Anhydride (5)

The title compound of Example 2 (28.2 g, 139.5 mmol) was suspended in 90 ml of acetic anhydride and heated to reflux for 2 hours. The reaction was evaporated to dryness to give 24.4 g of the title compound as crude product (95% yield). $^1$H NMR(CDCI$_3$) : 7.73 (t). I.R.: 3025 (m), 1877 (m), 1794 (vs), 1505 (s) , 1220 (vs), 910 (s) , 780 (rs) cm$^{-1}$.

EXAMPLE 4

Hydroxylamine-2-Hydroxamic Acid-4.5-Difluorobenzoate (6)

Hydroxylamine hydrochloride (19.24 g, 276.9 mmol) was added to sodium methoxide in methanol (6.37 g of Na metal in 250 ml of methanol), and heated gently to 45° C. over a period of 45 minutes. The reaction was then filtered and the filtrate was cooled to 0° C. and the title compound of Example 3 (17 g, 92.3 mmol) was added. The reaction was then allowed to warm to room temperature and stirred for 1 hour. The product was isolated via filtration and drying of the solids in vacuo to provide 17.5 g of the title compound (78% yield). M.P. 242°–245° C. (discoloration at 140° C.): $^1$H NMR(d6-DMSO) : 7.52 (q) ; 7.74(q).

EXAMPLE 5

4.5-Difluoroanthranilic Acid (9)

To the title compound of Example 4 (300 mg, 1.19 mmol) was added 5 ml of 10% NaOH solution and p-toluenesulfonyl chloride (0.5 g, 2.38 mmol) and the mixture was allowed to stir for 16 hours. The reaction was acidified to pH 4.5 with 10% HCl and the reaction was extracted with 3×20 ml of methylene chloride. The combined organic layers were dried over MgSO$_4$ and evaporated to give 176 mg of the title compound (85% yield). M.P. 178°–180° C. $^1$H NMR(d6-DMSO) : 6.72 (q); 7.60 ( q).

EXAMPLE 6

4,5-Difluoroanthranilic Acid (9)

To 4,5-dichlorophthalic anhydride (1.0 g, 4.61 mmol, M.W. 217) in 4 ml of dry sulfolane was added potassium fluoride (0.94 g, 16.1 mmol) and the reaction was heated to 185° C. for 2 hours. The reaction was then cooled to room temperature and hydroxyl amine hydrochloride (0.64g, 9.22 mmol, M.W. 69.5) was added as a solution in 4.6 ml of 3M KOH. The reaction was allowed to stir at room temperature for 2 additional hours. To this mixture was added more KOH (0.74 g) and p-toluenesulfonyl chloride (2.2 g, 11.53 mmol), and stirring was continued overnight. The pH of the reaction was adjusted to 12 with the KOH and the sulfolane was extracted with 4×15 ml portions of diisopropyl ether. The pH was then adjusted to 4 with 10% HCl solution and extracted with 4×15 ml of diisopropyl ether. The combined organic layers were dried and evaporated to provide 245 mg of the title compound (M.W. 171) (31% yield). M.P. 178°–180° C. $^1$H NMR(d6-DMSO) : 6.72 (q); 760 (q).

EXAMPLE 7

N-Hydroxy-4.5-Difluorophthalamide (8)

The title compound of Example 4 (400 mg, 1.6 mmol) was heated under aspirator vacuum to 180° C. for 45 minutes. The product was collected via sublimation and 203 mg of the title compound as pure material was isolated (64% yield). $^1$H NMR(D6-DMSO) : 8.04 (t).

EXAMPLE 8

4,5-Difluoroanthranilic Acid (9)

The title compound of Example 7 (100 mg, 0.5 mmol) was suspended in 5 ml of 10% NaOH solution and p-toluenesulfonyl chloride (105 mg, 0.55 mmol) was added and the solution was allowed to stir for 16 hours. The pH of the reaction solution was then adjusted to 4.5 with 10% HCl and the title compound was extracted with 3×25 ml of methylene chloride. The combined organic layers were dried over MgSO$_4$ and evaporated to give 60 mg of the title compound (69% yield). M.P. 178°–180° C. $^1$H NMR(d-DMSO) : 6.72 (g); 7.60 (q).

EXAMPLE 9

2-Chloro-4,5-Difluorobenzate Acid (10)

A mixture of 12.2 g of anhydrous copper (II) chloride and 12.4 g of t-butyl nitrite in 360 ml of anhydrous acetonitrile was cooled to 0° C. and stirred rapidly as 13.7 g of title compound of either Example 5, 6, or 8 (all the same compound) (80.12 mmol) was added in portions over a period of 5 minutes. After 2 hours at 0° C. the reaction was warmed to room temperature and allowed to stir overnight. The solvent was then evaporated to half the original volume and 200 ml of 6M HCl solution was added. The product was extracted with 60 ml of isopropyl ether and was purified by adding 10% KOH solution to the ether extracts. Acidification of the aqueous layer to pH 2 with 10% HCl and extracting the clean product with 50 ml of isopropyl ether provided 11.5 g of the title compound as a solid (M.P. 86°–88° C. 75% yield) M.P. 86°–88° C. $^1$H NMR(d6-DMSO) : 7.35 (q); 7.92 (q).

I claim:

1. A method of preparing the compound of the formula

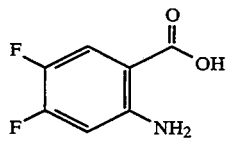

comprising reacting the compound of the formula

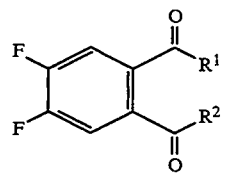

wherein R$^1$ and R$^2$ are taken together to form the group

O with hydroxylamine to form a first reaction solution and reacting the first reaction solution with an alkyl or aryl sulfonyl chloride and excess base.

2. The method of claim 1, wherein said alkyl or arylsulfonyl chloride is p-toluenesulfonyl chloride.

3. The method of claim 1, wherein said base is an alkali metal or alkaline earth metal base.

4. The method of claim 3, wherein said alkali metal or alkaline earth metal base is selected from the group consisting of NaOH, KOH, LiOH, Ca(OH)$_2$, and CsCO$_3$.

5. The method of claim 1, wherein said method is performed in one reaction vessel.

* * * * *